(12) United States Patent
Bell et al.

(10) Patent No.: US 6,179,872 B1
(45) Date of Patent: Jan. 30, 2001

(54) BIOPOLYMER MATT FOR USE IN TISSUE REPAIR AND RECONSTRUCTION

(75) Inventors: Eugene Bell, Boston; Tracy M. Sioussat, Reading; Michael J. Begley, Somerville, all of MA (US)

(73) Assignee: Tissue Engineering, South Boston, MA (US)

(*) Notice: Under 35 U.S.C. 154(b), the term of this patent shall be extended for 0 days.

(21) Appl. No.: 09/042,549

(22) Filed: Mar. 17, 1998

(51) Int. Cl.⁷ ............................. A61L 31/00; A61L 27/00
(52) U.S. Cl. .................... 623/11.11; 623/16; 530/354; 530/356; 442/123; 428/304.4
(58) Field of Search .................... 530/356, 354; 623/11, 16, 11.11; 442/123; 428/304.4

(56) References Cited

U.S. PATENT DOCUMENTS

| | | | |
|---|---|---|---|
| 4,066,083 | 1/1978 | Ries | 128/325 |
| 4,233,360 | * 11/1980 | Luck et al. | 428/310 |
| 4,606,337 | 8/1986 | Zimmermann et al. | 128/156 |
| 4,789,663 | * 12/1988 | Wallace et al. | 514/21 |
| 4,839,215 | * 6/1989 | Starling et al. | 428/131 |
| 5,002,583 | * 3/1991 | Pitaru et al. | 623/66 |
| 5,263,983 | 11/1993 | Yoshizato et al. | 623/12 |
| 5,723,007 | 3/1998 | Engel et al. | 623/11 |

FOREIGN PATENT DOCUMENTS

| | | |
|---|---|---|
| 2 657 352 | 7/1991 | (FR) . |
| WO 9210217 | 6/1992 | (WO) . |
| WO 9615818 | 5/1996 | (WO) . |

* cited by examiner

*Primary Examiner*—Daniel Zirker
(74) *Attorney, Agent, or Firm*—Lahive & Cockfield, LLP

(57) ABSTRACT

Biopolymer matt, biopolymer matt composites, biopolymer matt compositions, and methods of preparing the matt and composite matts are described. Also described are biocompatible constructs which include extracellular matrix macromolecules and methods of preparing these constructs. The matt, matt compositions and biocompatible constructs of the invention can be used in tissue repair and reconstruction.

13 Claims, No Drawings

BIOPOLYMER MATT FOR USE IN TISSUE REPAIR AND RECONSTRUCTION

BACKGROUND OF THE INVENTION

Collagen scaffolds have been used in tissue repair and tissue reconstruction. The scaffolds are usually crosslinked to provide the degree of wet strength and measured resistance to dissolution needed for these applications. In general, the crosslinking of collagen sponges or foams reduces or degrades the normal binding sites to which cells and certain molecules secreted by cells attach. Furthermore, collagen sponges, gelatin sponges or collagen gels, while biologically active, lack biological activity typically present in the extracellular matrix environment due to the lack of non-collagen components and thus information which binds to collagen or to non-collagen components themselves. Because of their deficiencies, collagen scaffolds crosslinked by known methods induce little regeneration in vivo or serve poorly as histiotypic and organotypic models in vitro.

A need exists, therefore, for an improved biopolymer form that overcomes or minimizes the above-mentioned problems and preserves the natural structure of the collagen.

SUMMARY OF THE INVENTION

The invention features biopolymer scaffolds in the form of biopolymer matt or biopolymer matt composites, e.g., resorbable biopolymer matt, for membranous or thick tissue applications, or as a filler material for tissue repair and tissue reconstruction which has a high strength to unit volume even before crosslinking. The invention also features biopolymer matt compositions comprising biopolymer matt and various layers of biopolymer foams, biocompatible constructs comprising biopolymer matt and extracellular matrix macromolecules, and methods for making and using the biopolymer matt, biopolymer matt composites, biopolymer matt compositions, and biocompatible matt constructs.

The biopolymer matt and biopolymer matt compositions can be used in vitro, for example, as model systems for research, or in vivo as prostheses or implants to replace damaged or diseased tissues or to provide scaffolds which, when occupied by cells, e.g., host cells, are remodeled to become functional tissues. In either case, the matt, matt composites, and matt compositions can be seeded with cells, e.g., mammalian cells, e.g., human cells, of the same type as those of the tissue which the matt, matt composites, or matt compositions is used to repair, reconstruct, or replace. Examples of tissues which can be repaired and/or reconstructed using the matt, matt composites, and matt compositions described herein include nervous tissue, skin, vascular tissue, cardiac tissue, pericardial tissue, muscle tissue, ocular tissue, periodontal tissue, connective tissue such as bone, cartilage, tendon, and ligament, organ tissue such as kidney tissue, and liver tissue, glandular tissue such as pancreatic tissue, mammary tissue, and adrenal tissue, urological tissue such as bladder tissue and ureter tissue, and digestive tissue such as intestinal tissues.

In one aspect of the invention, the matt, matt composites, and matt compositions seeded with tissue specific cells are introduced into a recipient, e.g., a mammal, e.g., a human. Alternatively, the seeded cells which have had an opportunity to organize into a tissue in vitro and to secrete tissue specific biosynthetic products such as extracellular matrix proteins and/or growth factors which bond to the matt and matt compositions are removed prior to implantation of the matt or matt compositions into a recipient.

Accordingly, the invention pertains to biopolymer matts having selected characteristics. In another aspect of the invention, the biopolymer matt comprises a densely packed random array of biopolymer fibrils and has a high strength to unit volume and preserves the native structure of the biopolymer fibrils. Examples of molecules which can form biopolymer fibrils which can be used in the biopolymer matt include collagen, laminin, elastin, fibronectin, fibrinogen, thrombospondin, gelatin, polysaccharides, poly-1-amino acids and combinations of biopolymers. A preferred molecule for biopolymer production is collagen, e.g., porcine fetal collagen. In other embodiments, the biopolymer matt can include macromolecules necessary for cell growth, morphogenesis, differentiation, or tissue building and combinations thereof, extracellular matrix particulates and/or cells.

Biopolymer matt of the invention can be prepared by forming a biopolymer solution in which fibril formation occurs, e.g., collagen fibril formation, pouring the solution over a porous structure which traps and/or embeds the fibrils and forms a semisolid fibril-gel structure which can be dried to a thin, dense fibrillar membrane, e.g., a matt. In another embodiment, the addition of sodium chloride in the neutralization buffer diminishes the gel component resulting in a higher concentration of fibrils.

In another aspect of the invention, matt composites can be formed by collecting sequential layers of fibril slurry on the porous support.

In yet another aspect of the invention, the porosity of the matt can be manipulated by various physical or chemical methods. In still another aspect of the invention, the strength of the biopolymer matt can be manipulated by various physical or chemical methods.

In yet an additional aspect of the invention, the biopolymer matt, matt composite, or matt composition can further be conditioned with cells prior to use in vitro or in vivo. Cell conditioning is an application-specific method used to speed integration of the matt, matt composite, or matt composition into its new function, to speed recovery of repair tissue and to direct authentic replacement of the damaged or missing tissue. Biopolymer matt, biopolymer matt composites, or biopolymer matt compositions can be used as a substrate for the growth of cells appropriate for the site of use. For example, for a biopolymer matt, biopolymer matt composite, or biopolymer matt composition used to repair bone defects as a periosteum, the conditioning cells would include, e.g., osteoblasts. For a biopolymer matt, biopolymer matt composite, or biopolymer matt composition used as pericardial membrane, the conditioning cells would include, e.g., mesothelial cells. For a biopolymer matt, biopolymer matt composite, or biopolymer matt composition used in the abdomen, the conditioning cells would include, e.g., mesothelial cells.

During conditioning, cells residing on biopolymer matt, biopolymer matt composite, or biopolymer matt composition deposit onto the matt, matt composite, or matt composition, macromolecules, such as protein products recognizable by the cells neighboring the defect at the site of matt, matt composite, or matt composition placement. The cell choice and thus the protein products can direct two things. They can direct the migration of the neighboring cells onto the matt, matt composite, or matt composition and the remodeling of the matt, matt composite, or matt composition material to replace the matt, matt composite, or matt composition with authentic covering tissue or the cell products will stimulate the regrowth of the tissue desired beneath the matt, matt composite, or matt composition while other cells remodel the matt, matt composite, or matt composition from the opposite side. After a period of time for the conditioning cells to deposit sufficient signaling and extracellular matrix molecules onto the matt, matt composite, or matt composition, the matt, matt composite, or matt compositions can be used as living implants to serve as living tissue equivalents or model tissue systems. Alternatively, cells of the matt, matt composite, or matt compositions can be killed by freezing or freeze drying the construct. Freeze drying eliminates living material, but leaves the deposited proteins in their natural states.

The biopolymer matt can be used alone, e.g., as a collagenous membrane for a periodontal barrier, or as a periosteal barrier to aid in bone repair. The biopolymer matt can also be used as a biopolymer composite by collecting sequential layers of different fibril slurry on the porous support and fusing these layers to each other. The biopolymer matt or biopolymer matt composites can also be used as a matt composition comprising a biopolymer matt and a biopolymer foam, e.g., as in the tissue repair of dura mater of the central nervous system. For example, a single density foam can be cast onto a finished matt to yield a structure with two layers of distinct characteristics, the matt layer of high density and low to no porosity and the foam layer with low density and high porosity. Single and double density biopolymer foams are described in U.S. Ser. No. 08/754,818, filed Nov. 21, 1996, the contents of which are incorporated herein by references in their entirety. Such implant sites consisting of compound tissue can be treated with matt compositions which include epi- meso- or endothelial cells on a matt surface and mesenchymal cells in the foam scaffold. For these applications, the low porosity matt side can minimize adhesions or fluid loss on one surface and the high porosity side can attract and support cell growth and differentiation required for healing. To further protect against adhesions or fluid loss in these applications and in applications requiring the use of matt alone, one can modify the surface of the matt. Modification can be accomplished biologically by growing and differentiating keratinocytes on one side of the matt to produce a stratum corneum. Matt compositions comprising one or more layers of biopolymer matt or biopolymer matt composites and more than one layer of single or double density biopolymer foams are also specifically contemplated herein.

As mentioned above, the matt can incorporate fiber structures, such as a single fibers, braids, or fabrics to achieve general reinforcement, directed reinforcement or to achieve directional cell growth. Examples of implants requiring such structures include skeletal replacements or temporary reinforcing structures. The matt can be cast in shapes other than sheets. It can be cast as tubes or orbs, such as spheres, to produce membranous structures which can contain material or liquids for specialized functions. Examples of implants made from matt, matt composite, or matt compositions include, for example, vessels, ducts, ureters, bladders and bone implants from matt cylinders filled with bone replacement material.

A matt composition comprising a matt and a single density foam, either with or without cell seeding, which is not freeze dried, can be used to build living tissue equivalents or model tissue systems. An example of this is the growth of dermal fibroblasts in the single density foam and the differentiated growth of keratinocytes on the porous surface matt layer for a skin model or a living implant system which quickly replaces lost function in critical situations and which can be cryopreserved for storage stockpiling. If not desired as a living implant system, the cell-laden developed complex can be freeze dried for later use as an implant which directs host tissue regrowth through information derived from the material the cultivated cells deposit onto the structures prior to freeze drying.

DETAILED DESCRIPTION OF THE INVENTION

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention features biopolymer matt, biopolymer matt composites, biopolymer matt compositions comprising biopolymer matt and biopolymer foam, biocompatible constructs comprising biopolymer matt and extracellular matrix macromolecules, and methods for making and using the matt, matt composites, and matt compositions. The biopolymer matt, matt composites, and mat compositions, in their native fibril structure, contain information to induce the repair or regeneration of damaged, diseased or missing tissue. Additional information for repair or regeneration can be added by mixing other informational macromolecules to the biopolymer matt, matt composites, and matt compositions. The biopolymer matt, matt composites, and matt compositions are fully resorbable when not reinforced by non-resorbable fibers and over time can be replaced by new normal pure host tissue. The biopolymer matt, matt composites, and matt compositions are more resistant to enzymatic breakdown than other collagen products of high information content, such as gels or foams. The biopolymer matt, matt composites, and matt compositions can be produced under physiological conditions, so living cells can be incorporated throughout the structure and on the completed form, thus yielding a living implant. The information content of the biopolymer matt, matt composites, and matt compositions can induce authentic healing and repair. For example, a living cell matt can replace the missing host tissue and its function immediately, and still be remodeled by authentic host tissue gradually with no interruption of tissue function. The biopolymer matt, matt composites, and matt compositions can be produced in a manner which gives them more strength than other collagen products of high information content. Therefore, they can be used in situations which requires an implant of strength.

A biopolymer is a naturally occurring polymeric substance formed from individual molecules in a biological system or organism. Biopolymers can also be man-made by manipulation of the individual molecules once obtained outside the biological system or organism. The biopolymer is suitable for introduction into a living organism, e.g., a mammal, e.g., a human. The biopolymer is non-toxic and bioabsorbable when introduced into a living organism and any degradation products of the biopolymer should also be non-toxic to the organism. The biopolymers of the invention can be formed into biocompatible forms, e.g., matt, matt composites, matt compositions, including biocompatible foams, biocompatible gels, biocompatible constructs which include biocompatible fibers, e.g., collagen fibers, biocompatible fabrics, e.g., collagen fabrics, all with or without other extracellular matrix macromolecules. Examples of molecules which can form biopolymers and which can be used in the present invention include collagen, laminin, elastin, fibronectin, fibrinogen, thrombospondin, gelatin, polysaccharides, poly-1-amino acids and combinations thereof. In one embodiment, a combination or mixture of one or more biopolymers can be used to form the biocompatible forms, e.g., fibers, matt, and matt compositions of the invention. For example, a combination of laminin and type IV collagen can be used to form the biopolymer fibers described herein. A preferred molecule for biopolymer production is collagen.

Preferred sources of molecules which form biopolymers include mammals such as pigs, e.g., near-term fetal pigs, sheep, fetal sheep, cows, and fetal cows. Other sources of the molecules which can form biopolymers include both land and marine vertebrates and invertebrates. In one embodiment, the collagen can be obtained from skins of near-term, domestic porcine fetuses which are harvested intact, enclosed in their amniotic membranes. Collagen or combinations of collagen types can be used in the matt and matt compositions described herein. Examples of collagen or combinations of collagen types include collagen type I, collagen type II, collagen type III, collagen type IV, collagen type V, collagen type VI, collagen type VII, collagen type VIII, collagen type IX, collagen type X, collagen type XI, collagen type XII, collagen type XIII, and collagen type XIV. A preferred combination of collagen types includes collagen type I, collagen type III, and collagen type IV. Preferred mammalian tissues from which to extract the molecules which can form biopolymer include entire mammalian fetuses, e.g., porcine fetuses, dermis, tendon, muscle and connective tissue. As a source of collagen, fetal tissues are advantageous because the collagen in the fetal issues is not as heavily crosslinked as in adult tissues. Thus, when the collagen is extracted using acid extraction, a greater percentage of intact collagen molecules is obtained from fetal tissues in comparison to adult tissues. Fetal tissues also include various molecular factors which are present in normal tissue at different stages of animal development.

In a preferred embodiment, the biopolymer matt, matt composite, or matt composition is a collagen matt, collagen matt composite, or collagen matt composition. Collagen solutions can be produced by salt extraction, acid extraction, and/or pepsin extraction from the starting material. In a preferred embodiment, the collagen used is produced by sequentially purifying two forms of collagen from the same collagen-containing starting material. First, intact collagen is acid extracted from the starting material, the extract is collected and collagen is prepared as a collagen solution, e.g., by precipitating the collagen with sodium chloride and solubilizing the collagen in a medium having an acidic pH. Meanwhile, truncated collagen, i.e., collagen from which the telopeptides have been cleaved or partly cleaved leaving only the helical portion or the helical portion with some telopeptides, is extracted from the starting material using enzyme, e.g., an enzyme which is functional at an acidic pH, e.g., pepsin, extraction. Then, the collagen from this pepsin extract is purified separately by similar methods as from the first extract.

The biopolymers can be used to create matts, matt composites, or matt compositions which can be in any form or shape, e.g., strips, sheets, tubes, etc. In addition, the biopolymers can be used to create matts which can be supported by polymer mesh, e.g., a teflon mesh, or used with tissue culture inserts for multiwell plates which can be used as molds in which matt, matt composites, and matt compositions of the invention can be formed on the polycarbonate membrane of the insert. Polymer meshes used with the matt, matt composites, and matt compositions of the invention can expose cells contained on and within the matt, matt composites, and matt compositions to the atmosphere as, for example, when the matt, matt composites, and matt compositions are used as skin equivalents to stimulate formation of a stratum corneum. Both the meshes and culture inserts have the advantage of providing a means for handling the matt, matt composites, and matt compositions without requiring actual contact with the matt, matt composites, or matt compositions. The forms and shapes in which the matt, matt composites, and matt compositions are made can mimic those of tissues or body parts to be replaced and thus can be used as prostheses or grafts which tissue cells remodel to promote regeneration of a replacement tissue in the recipient.

Macromolecules necessary for cell growth, morphogenesis, differentiation, and tissue building can also be added to the biopolymer molecules or to the biopolymer fibrils to further promote cell ingrowth and tissue development and organization within the matt. The phrase "macromolecules necessary for cell growth, morphogenesis, differentiation, and tissue building" refers to those molecules, e.g., macromolecules such as proteins, which participate in the development of tissue. Such molecules contain biological, physiological, and structural information for development or regeneration of the tissue structure and function. Examples of these macromolecules include, but are not limited to, growth factors, extracellular matrix proteins, proteoglycans, glycosaminoglycans and polysaccharides. Alternatively, the biopolymer matts, matt composites, and matt compositions of the invention can include extracellular matrix macromolecules in particulate form or extracellular matrix molecules deposited by cells or viable cells.

The term "growth factors" is art recognized and is intended to include, but is not limited to, one or more of platelet derived growth factors (PDGF), e.g., PDGF AA, PDGF BB; insulin-like growth factors (IGF), e.g., IGF-I, IGF-II; fibroblast growth factors (FGF), e.g., acidic FGF, basic FGF, β-endothelial cell growth factor, FGF 4, FGF 5, FGF 6, FGF 7, FGF 8, and FGF 9; transforming growth factors (TGF), e.g., TGF-P1, TGF-β1.2, TGF-β2, TGF-β3, TGF-β5; bone morphogenic proteins (BMP), e.g., BMP 1, BMP 2, BMP 3, BMP 4; vascular endothelial growth factors (VEGF), e.g., VEGF, placenta growth factor; epidermal growth factors (EGF), e.g., EGF, amphiregulin, betacellulin, heparin binding EGF; interleukins, e.g., IL-1, IL-2, IL-3, IL-4, IL-5, IL-6, IL-7, IL-8, IL-9, IL-10, IL-11, IL-12, IL-13, IL-14; colony stimulating factors (CSF), e.g., CSF-G, CSF-GM, CSF-M; nerve growth factor (NGF); stem cell factor; hepatocyte growth factor, and ciliary neurotrophic factor. The term encompasses presently unknown growth factors that may be discovered in the future, since their characterization as a growth factor will be readily determinable by persons skilled in the art.

The term "extracellular matrix proteins" is art recognized and is intended to include one or more of fibronectin, laminin, vitronectin, tenascin, entactin, thrombospondin, elastin, gelatin, collagens, fibrillin, merosin, anchorin, chondronectin, link protein, bone sialoprotein, osteocalcin, osteopontin, epinectin, hyaluronectin, undulin, epiligrin, and kalinin. The term encompasses presently unknown extracellular matrix proteins that may be discovered in the future, since their characterization as an extracellular matrix protein will be readily determinable by persons skilled in the art.

The term "proteoglycan" is art recognized and is intended to include one or more of decorin and dermatan sulfate proteoglycans, keratin or keratan sulfate proteoglycans, aggrecan or chondroitin sulfate proteoglycans, heparan sulfate proteoglycans, biglycan, syndecan, perlecan, or serglycin. The term encompasses presently unknown proteoglycans that may be discovered in the future, since their characterization as a proteoglycan will be readily determinable by persons skilled in the art.

The term "glycosaminoglycan" is art recognized and is intended to include one or more of heparan sulfate, chondroitin sulfate, dermatan sulfate, keratan sulfate, hyaluronic acid. The term encompasses presently unknown glycosaminoglycans that may be discovered in the future, since their characterization as a glycosaminoglycan will be readily determinable by persons skilled in the art.

The term "polysaccharide" is art recognized and is intended to include one or more of heparin, dextran sulfate, chitin, alginic acid, pectin, and xylan. The term encompasses presently unknown polysaccharides that may be discovered in the future, since their characterization as a polysaccharide will be readily determinable by persons skilled in the art.

Suitable living cells include, but are not limited to, epithelial cells, e.g., keratinocytes, adipocytes, hepatocytes, neurons, glial cells, astrocytes, podocytes, mammary epithelial cells, islet cells; endothelial cells, e.g., aortic, capillary and vein endothelial cells; and mesenchymal cells, e.g., dermal fibroblasts, mesothelial cells, stem cells, osteoblasts, smooth muscle cells, striated muscle cells, ligament fibroblasts, tendon fibroblasts, chondrocytes, and fibroblasts.

As used herein, the term "matt" refers to a biopolymer scaffold comprising a densely packed random array of biopolymer fibrils or bundles of fibrils or particles, e.g., collagen fibrils. Matts which have been dried, as discussed previously, possess a wet tensile strength of at least 0.02 MPa with a preferred strength of greater than 1 MPa and have a collagenase resistance of at least 20 min per mg of collagen at a collagenase concentration of 10 units per 1 cm$^2$ of product. Typically the fibrils or bundles of fibrils are between about 0.01 $\mu$m and 50 $\mu$m in diameter and between about 0.0002 and 5.0 mm in length, preferably 0.1 $\mu$m to 20 mm wide and 0.01 mm to 3 mm long. Matts, whether dried or not, possess the following characteristics: (1) physically stable in aqueous solutions; (2) nontoxic to living organisms; (3) can serve as a substrate for cell attachment and growth; (4) approximately 0.01 mm to 20 mm thick, preferably 0.1 to 5.0 mm thick.

As used herein, the term "fibrils" refers to ordered multimers of molecules which create a fibrous overall structure. In the case of collagen fibrils, the collagen molecules are arranged in a quarter stagger, where each side-by-side association of molecules has an orderly shift of 25% (the bead of one collagen molecule is arranged to be juxtaposed to the adjacent molecule 25% down the chain of that molecule). Fibrils, especially those of collagen often have a characteristic appearance by electron microscopy. Fibrils associate into bundles. Higher multiples of fibril bundles are fibers.

The term "matt composite" refers to a biopolymer form comprising sequential layers of biopolymer matt which are bonded to each other.

The term "matt composition" refers to a biopolymer composition comprising a matt, e.g., a biopolymer matt which is preferably resorbable, and optionally, one or more biopolymer foams, e.g., a single or double density foam. Single and double density biopolymer foams are described in U.S. Ser. No. 08/754,818, filed Nov. 21, 1996, the contents of which are incorporated herein by references in their entirety.

The biopolymer foams can be single density or double density foams. As used herein, the term "foam" refers to a network of communicating microcompartments having biopolymer molecules and/or biopolymer filaments interspersed within the walls of the microcompartments. The language "single density foam" refers to a biopolymer foam having at least two of the following characteristics: 1) it has microcompartments with the volume dimensions of x, y, and z wherein x=length, y=width, and z=height and are substantially equal. Typically, x, y, and z range from about 1 $\mu$m to about 300 $\mu$m, preferably from about $\mu$m to about 200 $\mu$m, more preferably from about 40 $\mu$m to about 150 $\mu$m, and most preferably from about 50 $\mu$m to about 100 $\mu$m; 2) it has microcompartments with an average wall thickness of less than about 10 $\mu$m; 3) it has microcompartments with walls which include biopolymer fibers and/or filaments; 4) it is physically stable in aqueous solutions; 5) it is nontoxic to living organisms; and 6) it can serve as a substrate for cell attachment and growth. The single density foams retain their structure when hydrated, for example, in aqueous buffer solution or tissue culture medium. In addition, the three dimensional structure of the single density foams can support the organization of cells seeded into them. Single density foams, when prepared from collagen and without cells, can be readily digested with collagenase, e.g., 0.1% collagenase. Examples of molecules which can form biopolymers which can be used in the single density biopolymer foams include collagen, alginic acid, polyvinyl alcohol, elastin, chondroitin sulfate, laminin, fibronectin, fibrinogen, and combinations of these biopolymers. A preferred biopolymer is collagen, e.g., porcine fetal collagen. In other embodiments, the single density biopolymer foams can include extracellular matrix particulates and/or cells.

As used herein, the language "double density foam" refers to a biopolymer foam having at least two of the following characteristics: 1) it has microcompartments with the volume dimensions of x, y, and z wherein x=length, y width, and z=height, two of which are substantially equal and the third of which is decreased or diminished by a factor of at least about 10, and more preferably at least about 20 or more compared to the same dimension in the single density foam, and can range from about 1 $\mu$m to about 300 $\mu$m, preferably from about 20 $\mu$m to about 200 $\mu$m, more preferably from about 40 $\mu$m to about 150 $\mu$m, and most preferably from about 50 $\mu$m to about 100 $\mu$m; 2) it has microcompartments with an average wall thickness of less than about 10 $\mu$m; 3) it has microcompartments with walls which include biopolymer fibers and/or filaments; 4) it is physically stable in aqueous solutions; 5) it is nontoxic to living organisms; and 6) it can serve as a substrate for cell attachment and growth. The double density foams, when prepared from collagen, are resistant to collagenase digestion to a greater degree than single density foams made from collagen, e.g., from about 3 to about 5 times or more, more resistant to 0.1% collagenase than single density foams. Double density foams prepared from collagen also have a higher collagen density per unit volume than the collagen content per unit volume of single density foams. When hydrated, the height of the double density foams is typically from about 0.2 mm to about 0.4 mm. Either surface of the double density foam provides a substrate suitable for plating epithelial, endothelial, and mesothelial cells which can form sheets. Mesenchymal cells can also be seeded onto the double density foams. The double density foams can be produced in the same sizes and same forms, e.g., in any form and in combination and bonded to a polymer mesh or as a multiwell plate insert, as the single density foams. Cells grown on both the single and double density foams of the invention have morphologies characteristic of cells of three dimensional tissues and can form normal intercellular relationships, i.e., intercellular relationships like those in the tissue from which they are derived or obtained. Preferred biopolymers for use in double density foams are described above as in single density foams. In other embodiments, the double density biopolymer foams can include extracellular matrix particulates and/or cells.

Either the surface of the matt, matt composites, or matt compositions can provide a substrate suitable for plating epithelial, endothelial, and mesenchymal cells which can be formed into sheets or other articles. Cells can also be seeded onto single or double density foams. Cells grown on biopolymer matts and biopolymer matt compositions have morphologies characteristic of cells of three dimensional tissues and can form normal intercellular relationships, i.e., intercellular relationships like those in the tissue from which they are derived or obtained.

The biopolymer matt of the invention can be produced by diluting a solution of molecules which can form biopolymers, e.g., collagen, elastin, laminin, fibronectin, poly-1 amino acids, fibrinogen, gelatin, polysaccharides, thrombospondin and combinations of these biopolymers. Preferably, the biopolymer collagen, more preferably, porcine fetal collagen is diluted to 0.1–10 mg/ml with a buffer, e.g., a 1 to 50 mM HEPES, TES or tris pH 7.4, 5 to 400 mM sodium or potassium phosphate, pH 7.4, the preceding buffers with or without 1 to 150 mM sodium chloride, a standard balanced salt solution or serum-free tissue culture medium. The pH then is finely adjusted to pH 7.4 using a dilute base, e.g., a sodium, ammonium or potassium hydroxide solution, preferably 5% ammonium hydroxide. The solution is incubated at a constant temperature (between 37 and 4° C., preferably 22° C.) while continuously gently mixing to allow for fibril formation. The fibrils generated are between about 0.01 and 50 $\mu$m wide and between about 0.0002 and 5.0 mm long. The fibril solution is poured over a porous structure, such as a screen or filter of approximately between about 800 and about 18 mesh count, preferably about 50 to 500 mesh count or having a porosity of approximately between about 15 to about 1000 $\mu$m, preferably about 25 to 280 $\mu$m or a fabric or a nonwoven or a foam, e.g., single density. The unpolymerized molecules transit through the porous structure and limited mesh porosity tops the fibrils from transmitting through. As the fibrils become trapped on and slightly below the top surface, their layering becomes dense enough to slow the flow of the solution through the mesh. The solution flow can be assisted by a light vacuum or by capillary wicking by applying an absorbent material to the opposite side of the porous structure. As the solution slows down, the remaining solution above the porous structure can be allowed to gel to trap the fibrils and form a semisolid fibril-gel structure from approximately between about 0.01 to about 2.0 cm, preferably about 0.01 to 0.5 cm thick.

In one aspect of the invention, the addition of sodium chloride in the neutralization buffer can cause the gel component to diminish and result in the collection of more fibrils. To accelerate the collection of fibrils, the incubated neutral collagen-fibril solution can be centrifuged at low speed, e.g., about 500–5000×g, preferably 1500×g, for approximately 2 to 30 minutes, preferably 5 minutes. The supernatant is discarded and the pelleted fibrils are resuspended to form a slurry. As a result of this modification, the matt structure can be built without the dependence of the draining properties of the screen. Therefore the fibril slurry can be transferred to solid bottom molds or onto double density foams or applied by centrifugal force or rotating motion to dishes and tubes.

In another embodiment of the invention, when the fibrils are formed or collected in a physiological buffer, such as phosphate buffered saline, balanced salt solutions, or serum-free tissue culture medium, living tissue cells may be included. These cells are mixed with the fibrils or the fibril slurry and are collected on the porous support within the matt. This matt then can be incubated in environments where the cells can survive and condition the matt in accordance with their characteristics.

In another embodiment of the invention, matt composites can be created. This is accomplished by collecting sequential layers of different fibril/fibril bundle slurries on the porous support. It can be done in a manner such that the layers bond to each other and impart new properties to the matt.

In still another embodiment of the invention, objects can be embedded in the matt to alter its texture or its tear properties. For some applications, handling and use of the matt can require a specific texture or tear resistance. Texture can be manipulated either by the surface characteristic of the porous support used to collect the fibrils or by embedding textured objects within the matt structure upon matt formation. Tear resistance can be manipulated by materials embedded in the matt or by the characteristics of the matt composites. Biocompatible particles in any shape which resist solubilization in physiological buffers can be used, e.g., beads of calcium phosphates, calcium sulfates, fibers of calcium sulfates, fragments of resorbable polymers, beads of gelatin or agarose. While calcium sulfate is used to create pores on the basis of its solubility as described below, the distinction for the use of calcium sulfate for the use of manipulation of the matt's tear properties is that the solubility in water, used for creating pores is great, while the solubility of calcium sulfate in physiological buffers, e.g., phosphate-buffered saline, is low. The presence of the particles in the finished matt acts as a stop around which a tear must travel in order to propagate. The sinuous route required by the tear due to the presence of the particles decreases the probability of tear propagation.

If immediate cell seeding is not desired, the trapped material on the porous structure is allowed to dry as deposited or pressed between porous absorbent material for flatness and the finished matt may be peeled away as a thin, dense fibrillar membrane.

In another embodiment, the porosity of the matt can be increased by aerating the fibril slurry with bubbles before drying. In an additional embodiment, porosity can be increased by vertically positioning through the support, e.g., a screen, fine inert filaments, e.g., wire filaments, at desired intervals. The fibrils will deposit around the filaments, which, after matt drying, can be removed to leave pores. In still another embodiment, porosity can be increased by treating the semisolid fibril-gel structure with a solution, such as an ethanol solution or a buffer slightly lower than neutrality to wash through the screen the collagen contributing to the gel and leaving only the fibrils on the screen, with the interfibril distance resulting in porosity. In yet another embodiment, porosity can be increased by freeze-drying the semisolid fibril-gel to retain the three-dimensional structure of the semisolid while removing the water and leaving gaps in water's place. In still an additional embodiment, porosity can be increased by physically boring perforations into the finished matt by the use of pins or a laser beam.

In yet an additional embodiment, porosity can be increased by mixing into the fibril slurry objects of approximately between about 0.002 to about 2.00 mm, preferably between about 0.01 to about 1.0 mm diameter which can be removed from the finished matts, with the pores left in the spaces formerly occupied by the objects. Examples of these objects include, e.g., ferrous particles, e.g., minute ball bearings or iron beads, which can be removed by magnets contacting a re-wetted matt; calcium sulfate, salt or sugar particles, which can be removed by soaking the dried matt in water; beads of gelled alginic acid, which can be removed by soaking the dried matt in EDTA at a concentration of approximately 2 to 1000 mM, preferably 20 to 200 mM; beads of agarose or waxes, which can be removed by subjecting the matt to moderate increases in temperature or washes in alcohol; and beads of gelatin, which can be removed by non-specific proteases, a process which can occur over time in the finished matt product through the action of living cells. Other methods for generating porosity in a matt are well known to those having skill in the art.

The use of alginic acid to increase the matt porosity results in a porous material which also holds water and can become a network of interconnecting pores in a sponge-like structure. Various macromolecules, when added to the collagen or the fibril slurry can either become bound to the collagen or trapped in the fibril network to impart the matt with porosity and water holding capacity. Proteins, such as gelatin; polysaccharides, such as pectins, xylan, heparin, dextran sulfate, chitin, alginic acid; glycosaminoglycans, in particular heparan sulfate, chondroitin sulfate, dermatan sulfate, and keratan sulfate and hyaluronic acid; and the proteoglycans containing the glycosaminoglycans, including decorin, keratan, heparan sulfate, syndecan, biglycan, perclean, aggrecan, serglycin, etc. are examples of substances which display these properties for the above applications. Preferred substances include gelatin and/or the glycosaminoglycans in proportions of approximately 0.1 to 4,000%, preferably 1–500% gelatin and/or glycosaminoglycan dry weight per dry weight of collagen.

In another embodiment, the strength of the matt can be increased by laying reinforcing material into the fibril collection. Such reinforcing materials include fibers, threads, e.g., braided threads, and/or fabrics, e.g., woven or nonwoven fabrics, prepared, for example, by textile methods and made from biopolymers, resorbable polymers, or non-resorbable polymers. Biopolymer fibers can be prepared by extruding the biopolymer in solution into a coagulation bath and transferring the biopolymer to a bath containing ethanol or acetone or another dehydrating solution. Alternatively, the fiber can be dehydrated by subjection to vacuum-drying. The biopolymer fiber can then be crosslinked by, for example, methods described in U.S. Ser. No. 08/754,818, filed Nov. 21, 1996, the contents of which are incorporated herein by references in their entirety. An example of an apparatus for spinning and processing a biopolymer fiber, e.g., collagen fiber, is described in U.S. Ser. No. 08/333,414, filed Nov. 2, 1994, the contents of which are incorporated herein by references in their entirety. The fibers can then be dried, spooled, for example, by pulling the moving fiber over more rollers, stretching and drying it and then winding it onto spools. The fibers can be woven, knitted, bundled or braided into fabric or other complex forms or constructs by textile methods for use as described herein.

Biopolymer nonwoven fabrics are typically composed of a collection of entangled biopolymer fibers of a selected size and density. Typically, the nonwoven biopolymer fabrics are produced by spooling dry biopolymer fiber onto a drum of circumference equal to that of the length of an individual fiber element. Spooling is continued until the number of wraps of fiber on the drum equals the number of pieces of fiber required for the fabric. A cut is then made across the wound fiber in a direction parallel to the drum axis and the fibers are removed from the drum. The fiber can then be crosslinked if it has not been previously crosslinked. The fiber is then dispersed in a volume of a phosphate buffer solution for a period of time to decrease its pH and soften the fiber. The fiber is transferred to a volume of water and agitated mechanically to produce entanglement of the fiber strands. The entangled fiber strands are sieved from the water onto a collection screen until they coat the screen in a mat of uniform density. The nonwoven fabric is then dried on the screen or after transfer to another surface, screen, or cell culture device. If desired, the nonwoven mat can be cut or punched into smaller shapes after drying.

Examples of materials suitable for matt reinforcing fibers, beads, braids, bundles of fibers, fabrics and/or nonwovens are materials which form biopolymers, resorbable polymers and non-resorbable polymers. Materials for biopolymers include collagen, alginic acid, laminin, elastin, gelatin, fibronectin, fibrinogen, thrombospondin, polysaccharides, poly-1-amino acids and combinations thereof. Materials for resorbable polymers include poly-α-hydroxyesters such as poly-1-lactic acid and poly-1-glycolic acid, polydioxinone, polyvinyl alcohol, surgical gut and combinations thereof. Examples of materials for non-resorbable polymers include silk, nylon, polytetrafluoroethylene, polypropylene, polyesters, polyurethanes and combinations thereof. Further combinations for fibers can be made by casting resorbable polymer fibers on non-resorbable polymers or casting biopolymer fibers on resorbable or nonresorbable fibers. A preferred material is collagen, preferably fetal porcine collagen.

Examples of implants requiring such reinforced structures include skeletal replacement, hernia repair or temporary reinforcing structures. For example, to repair a rotator cuff, strong fibers or sutures, preferably resorbable sutures, can be embedded within the matt structure at the time of depositing the fibril slurry to enable high tension to be placed on the finished product in the direction of reinforcement. These structures are described further herein.

In another embodiment, after drying the reinforced matt structure, individual thin fibers of instructional biopolymers can be cast onto the outer surface. The addition of these fibers is not structural, but rather instructional, and determine the direction of cell growth and tissue repair from the migration of cells along the fibers.

In one embodiment, when the biopolymer is collagen, the collagen can be treated with an enzyme, e.g., lysyl oxidase which primes the collagen for crosslinking. Lysyl oxidase, which can be purified from a variety of sources including, for example, calf aorta, human placenta, chicken embryo epiphyseal cartilage, pig skin, (see Shackleton, D. R. and Hulmes, D. J. S. (1990) *Biochem. J* 266:917–919), and several locations in pig embryos, converts the $\epsilon$-amino group of lysine to an aldehyde. This aldehyde is a reactive functional group which spontaneously binds to other lysine $\epsilon$-amino groups or other aldehydes on other collagen molecules to form irreversible covalent crosslinks. The result is that collagen becomes insoluble. Lysyl oxidase can be added to the collagen solutions under conditions which allow for the aldehyde conversion of the lysines. The lysyl oxidase is then removed from the collagen solution and the collagen is processed as described herein during which the spontaneous crosslinks form. For example, during the processing of the collagen matt, e.g., during the polymerization step, the crosslinks spontaneously form as the concentration of collagen per unit volume increases. The lysyl-oxidase-mediated crosslink is strong, irreversible and is a linkage naturally found in collagen. Collagen crosslinked in this manner is insoluble and susceptible only to specific enzymatic attack during remodeling of tissues. Lysyl oxidase can also be used to crosslink collagen for use as matt and matt compositions as well as spun fibers, gels, etc.

In still another embodiment, the strength of the matt can be increased by standard collagen crosslinking methods using, e.g., ultraviolet, dehydrothermal, or chemical crosslinkers. Typical chemical crosslinkers include, for example, glutaraldehyde, formaldehyde, acrylamide, carbodiimides, such as those known in the art, e.g., 1-ethyl-3-(dimethyaminopropyl)carbodiimide, diones known to those skilled in the art, e.g., 2,5-hexanedione, diimidates, e.g., dimethylsuberimidate, or bisacrylamides, e.g., N,N'-methylenebisacrylamide. In yet another embodiment, the matt's load-bearing capacity can be manipulated by creating the matt in varying thicknesses by modifying the volume or concentration of fibril-containing solution poured onto the screen.

Biocompatible constructs which include biopolymer matt or biopolymer matt compositions of the invention and extracellular matrix macromolecules are also specifically contemplated herein. Extracellular matrix macromolecules in soluble or particulate form dispersed or suspended in a biopolymer solution can also be applied onto and/or into the matt and matt compositions of the invention, thereby forming a matt, matt composite, or matt composition having extracellular matrix macromolecules or particulates. As used herein, the language "particulate form of extracellular matrix" refers to a fragment of an extracellular matrix derived from a tissue source formerly having living cells but which has been processed to remove the cells and to retain noncellular extracellular matrix factors such as, for example, growth factors also proteins, proteoglycans, glycosaminoglycans necessary for cell growth, morphogenesis, and differentiation. Methods for forming extracellular matrix particulates for producing graft tissue are disclosed in U.S. patent application Ser. No. 07/926,885 abandoned, filed Aug. 7, 1992, U.S. patent application Ser. No. 08/302,087 (U.S. Pat. No. 5,893,888), filed Sep. 6, 1994, and U.S. patent application Ser. No. 08/471,535 (U.S. Pat. No. 5,800,537), filed Jun. 6, 1995. The teachings of U.S. patent application Ser. Nos. 07/926,885, 08/302,087, and 08/471,535 are incorporated herein by reference.

The methods for forming extracellular matrix particulates include freezing a tissue source, e.g., a connective tissue source, having living cells, whereby the living cells are disrupted to form cell remnants consisting of, for example, cytoplasmic and nuclear components. The tissue source is then processed, e.g., by grinding, washing and sieving, to remove the cytoplasmic and nuclear components without removing extracellular matrix including macromolecules necessary for cell growth, migration, differentiation, and morphogenesis. The extracellular matrix is freeze-dried and fragmented, e.g., cryomilled to produce particulates of defined sizes, to produce extracellular matrix particulates.

The extracellular matrix particulates can include extracellular matrix proteins. For example, extracellular matrix particulates obtained from skin include transforming growth factor β1, platelet-derived growth factor, basic fibroblast growth factor, epidermal growth factor, IGFI, bFGF, syndecan-1, decorin, fibronectin, collagens, laminin, tenascin, and dermatan sulfate. Extracellular matrix particulates from lung include PDGF, TGFPβ1, bFGF, VEGF syndecan-1, fibronectin, laminin, and tenascin. The extracellular matrix particulates can also include cytokines, e.g., growth factors necessary for tissue development. The term "cytokine" includes but is not limited to growth factors, interleukins, interferons and colony stimulating factors. These factors are present in normal tissue at different stages of tissue development, marked by cell division, morphogenesis and differentiation. Among these factors are stimulatory molecules that provide the signals needed for in vivo tissue repair. These cytokines can stimulate conversion of an implant into a functional substitute for the tissue being replaced. This conversion can occur by mobilizing tissue cells from similar contiguous tissues, e.g., from the circulation and from stem cell reservoirs. Cells can attach to the prostheses which are bioabsorbable and can remodel them into replacement tissues.

Growth factors necessary for cell growth are attached to structural elements of the extracellular matrix. The structural elements include proteins, e.g., collagen and elastin, glycoproteins, proteoglycans and glycosaminoglycans. The growth factors, originally produced and secreted by cells, bind to the extracellular matrix and regulate cell behavior in a number of ways. These factors include, but are not limited to, one or more of platelet derived growth factors (PDGF), e.g., PDGF AA, PDGF BB; insulin-like growth factors (IGF), e.g., IGF-I, IGF-II; fibroblast growth factors (FGF), e.g., acidic FGF, basic FGF, β-endothelial cell growth factor, FGF 4, FGF 5, FGF 6, FGF 7, FGF 8, and FGF 9; transforming growth factors (TGF), e.g., TGF-β1, TGF-β1.2, TGF-β2, TGF-β3, TGF-β5; bone morphogenic proteins (BMP), e.g., BMP 1, BMP 2, BMP 3, BMP 4; vascular endothelial growth factors (VEGF), e.g., VEGF, placenta growth factor; epidermal growth factors (EGF), e.g., EGF, amphiregulin, betacellulin, heparin binding EGF; interleukins, e.g., IL-1, IL-2, IL-3, IL-4, IL-5, IL-6, IL-7, IL-8, IL-9, IL-10, IL-11, IL-12, IL-13, IL-14; colony stimulating factors (CSF), e.g., CSF-G, CSF-GM, CSF-M; nerve growth factor (NGF); stem cell factor; hepatocyte growth factor, and ciliary neurotrophic factor. Adams et al., "Regulation of Development and Differentiation by the Extracellular Matrix" *Development* Vol. 117, p. 1183–1198 (1993) (hereinafter "Adams et al.") and Kreis et al. editors of the book entitled "Guidebook to the Extracellular Matrix and Adhesion Proteins," Oxford University Press (1993) (hereinafter "Kreis et al.") describe extracellular matrix components that regulate differentiation and development. Further, Adams et al. disclose examples of association of growth factors with extracellular matrix proteins and that the extracellular matrix is an important part of the microenvironment and, in collaboration with growth factors, plays a central role in regulating differentiation and development. The teachings of Adams et al. and Kreis et al. are incorporated herein by reference.

Extracellular matrix particulates can be obtained from specific tissues. The particulates have two kinds of informational properties. The first is their molecular diversity, and the second is their microarchitecture, both of which are preserved in the preparation of the microparticulates. The preferred associations among the different molecules of the extracellular matrix are also preserved in the preparation of the microparticulates.

The extracellular matrix plays an instructive role, guiding the activity of cells which are surrounded by it or which are organized on it. Since the execution of cell programs for cell division, morphogenesis, differentiation, tissue building and regeneration depend upon signals emanating from the extracellular matrix, three-dimensional scaffolds, such as collagen matt and collagen matt compositions, are enriched with actual matrix constituents, which exhibit the molecular diversity and the microarchitecture of a generic extracellular matrix, and of extracellular matrices from specific tissues.

To provide further cellular and molecular binding sites on the surfaces of the matt and matt compositions to replace, for example, binding sites which have been compromised as a result of crosslinking procedures, a coating process can precede or accompany the application of extracellular matrix macromolecules or particulates to the collagen matt. In addition, artificial microstructures, typically having a size in the range of between about 5 and 500 m, composed of a matrix polymer, such as collagen, combined with other proteins, proteoglycans, glycosaminoglycans, extracellular matrix enzymes, cytokines (including growth factors), and glycosides can be created in the form of wet or dry particulates that can be applied with the coating solution to the surfaces of the collagen matt or collagen matt compositions. The selected components can be chemically or electrostatically bound to the biopolymer or can be contained in the microparticulate lattice or in a dehydrated form of the lattice. Thus, the invention also pertains to methods for preparing collagen-coated matt and extracellular matrix macromolecule or particulate-coated matt. These methods typically include forming the selected type of biopolymer matt as described herein and applying a collagen solution or an extracellular matrix particulate solution to the matt, matt composite, or matt composition, thereby forming the collagen-coated or extracellular matrix macromolecular or particulate-coated biopolymer matt, matt composite, or matt compositions. In one embodiment, the collagen solution also includes extracellular matrix macromolecules or particulates.

The matt, matt composites, and matt compositions of the present invention can be used as substrates for cell growth in vitro and in vivo, e.g., for establishing research model systems. For example, in one embodiment, the matt, matt composites, and matt compositions can be seeded with abnormal cells to study disease states including cancer. In another embodiment, the matt, matt composites, and matt compositions can serve as diagnostic test models for determining chemotherapeutic strategies by selecting for agents capable of killing cancer cells cultivated in or on the matt, matt composites, or matt compositions. In yet another embodiment, the matt, matt composites, and matt compositions can be used to test the toxicity of various substances to which cells in or on the matt are exposed.

The biopolymer matt, matt composites, and matt compositions can be used as formed or can be cell-conditioned. Cell conditioning is an application-specific method to speed integration of the matt, matt composites, or matt composition into its new function, to speed recovery and to direct authentic replacement of the damage or missing tissue. Matt, matt composite, or matt composition material is used as a substrate for the growth of cells appropriate for the site of use. For example, for a matt, matt composite, or matt composition used to repair bone defects as a periosteum, the conditioning cells would include, e.g., osteoblasts. For a matt, matt composite, or matt composition used as pericardial membrane, the conditioning cells would include, e.g., mesothelial cells. For a matt, matt composite, or matt composition used in the abdomen, the conditioning cells would include, e.g., mesothelial cells.

During conditioning, cells residing on the matt, matt composite, or matt composition deposit onto the matt, matt composite, or matt composition protein products recognizable by the cells neighboring the defect at the site of matt, matt composite, or matt composition placement. The cell choice and thus the protein products can direct two things in an implant situation. They can direct the migration of the neighboring cells onto the matt, matt composite, or matt composition and the remodeling of the matt, matt composite, or matt composition material to replace the matt, matt composite, or matt composition with authentic covering tissue or the cell products will stimulate the regrowth of the tissue desired beneath the matt, matt composite, or matt composition while other cells remodel the matt, matt composite, or matt composition from the opposite side. After a period of time for the conditioning cells to deposit sufficient signaling and extracellular matrix molecules onto the matt, matt composite, or matt composition, the matt, matt composite, or matt compositions can be used as living implants serve as living tissue equivalents or model tissue systems.

Alternatively, the cells of the matt, matt composite, or matt compositions can be killed by freeze drying the construct. Freeze drying eliminates living material, but leaves the deposited proteins in their natural states. Before or after this, if necessary or desired, the matt, matt composite, or matt composition may be washed by various mild methods, dilute acids (0.001–0.1 M hydrochloric or acetic acid) or bases (0.001–0.1 sodium hydroxide), dilute nonionic (0.01 to 1.0% triton X-100) or zwitterionic detergents (0.005–0.10 M CHAPS, 3-([3-cholamidopropyl]-dimethylammonio)-1-propane-sulfonate), to eliminate intracellular components. If this optional washing step occurs after freeze drying, the matt, matt composite, or matt composition again will be freeze dried for packaging as a dry product.

The matt, matt composite, and matt compositions can also be used as prostheses which can be introduced or grafted into recipients, e.g., such as mammalian recipients, e.g., humans. For example, the matt, matt composites, and matt compositions can be used as a prosthesis or to reconstitute, for example, the following types of tissue: nervous tissue, skin, vascular tissue, muscle tissue, connective tissue such as bone, cartilage, tendon, and ligament, kidney tissue, liver tissue, and pancreatic tissue. Tissue cells seeded into the matt, matt composites, and matt compositions can be obtained from a mammal, e.g., a human. If not added during matt formation, tissue cells are delivered to the matt, matt composites, and matt compositions by first suspending the cells in small volumes of tissue culture medium. The tissue culture medium which contains the cells can then be applied in drops to the matt, matt composites, or matt compositions. Alternatively, the matt, matt composites, or matt compositions can be placed in a vessel which contains the tissue culture medium and cells in suspension and which shakes such that the tissue culture medium containing the cells is distributed throughout the matt, matt composites, or matt compositions. In another embodiment, tissue cells can be suspended in a biopolymer solution e.g., a collagen solution, at low concentrations, at a temperature of about 4° C. to 10° C., and at a pH of about 7.0. The solution containing the cells can then be delivered to the matt, matt composites, and matt compositions. As matt is warmed to 37° C., the biopolymer solution, e.g., collagen solution, forms a gel in the matt. As used herein, the term "gel" refers a network or mesh or biopolymer filaments together with an aqueous solution trapped within the biopolymer scaffold of biopolymer fibrils. An alginate gel for use as a delivery vehicle of cells to the matt, matt composites, or matt compositions of the invention can be produced by addition of calcium which causes polymerization at room temperature and at a neutral pH. Selected epithelial, endothelial, or mesothelial cells can then be plated onto the surface of the gel-filled matt, matt composite, or matt composition.

The biopolymer matt can be used alone, e.g., as a collagenous membrane for a periodontal barrier, or as a periosteal barrier to aid in bone repair. Alternatively, the biopolymer matt can be used in a biopolymer matt composition comprising a biopolymer matt and a biopolymer foam, e.g., as in the tissue repair of dura mater of the central nervous system, e.g., a single density foam can be cast onto the finished matt to yield a structure with two layers of distinct characteristics, the matt layer of high density and low to no porosity and the foam layer with low density and high porosity. Single and double density biopolymer foams are described in U.S. Ser. No. 08/754,818, filed Nov. 21, 1996, the contents of which are incorporated herein by references in their entirety. Implant sites requiring a compound tissue, e.g., skin made up of two tissues, the epidermis and the dermis, can be treated with matt compositions which include epi- meso- or endothelial cells on a matt surface and mesenchymal cells in the foam scaffold. For these applications, the low porosity matt side can minimize adhesions or fluid loss on one surface and the high porosity side can attract and support cell growth and differentiation required for healing. Modification can be accomplished, for example, biologically by growing and differentiating keratinocytes on one side of the matt to produce a stratum corneum. Matt compositions comprising one or more layers of biopolymer matt or biopolymer matt composites and more than one layer of single or double density biopolymer foams are also specifically contemplated herein.

As mentioned above, the matt can incorporate fiber structures, such as a single fibers, braids, bundles of fibers or fabrics to achieve general reinforcement, directed reinforcement or to achieve directional cell growth. Examples of implants requiring such structures include, e.g., skeletal replacements or temporary reinforcing structures.

The matt, matt composites, or matt compositions can be cast in shapes other than sheets. It can be cast as tubes or orbs, such as spheres, to produce membranous structures which can contain material or liquids for specialized functions. Examples of implants made from matt, matt composites, or matt compositions include, e.g., vessels, ducts, ureters, bladders and bone implants from matt cylinders filled with bone replacement material. As used herein, the term "bone replacement material" refers to material which can fill voids in bone and which can assist in bone repair. Examples of bone replacement material include, but are not limited to, autologous bone graft, bone powder, demineralized bone, calcium sulfates, and calcium phosphates, e.g., hydroxyapatites, brushites and octacalcium phosphate. A matt composition comprising a matt and a single density foam, either with or without cells, and which is not dried can be used to build living tissue equivalents or model tissue systems. An example of this is the growth of dermal fibroblasts in the single density foam and the differentiated growth of keratinocytes on the porous surface matt layer for a skin model or a living implant system which quickly replaces lost function in critical situations and which can be cryopreserved for storage stockpiling. If not desired as a living implant system, the cell-laden developed complex can be freeze dried for later use as an implant which directs host tissue regrowth through information derived from the material the cultivated cells deposit onto the structures prior to freeze drying as described for cell conditioning above.

The matt, matt composites, and matt compositions of the invention can also be formed into vascular prostheses in the form of a tube and can be seeded internally with smooth muscle cells delivered in a neutralized collagen solution that gels after delivery, externally with adventitial fibroblasts and on its luminal surface with endothelial cells. For example, a tubular matt can be formed by dispensing biopolymer fibril slurry into a tube whose inner diameter is the outer diameter of the desired matt. The tube is rolled continuously while the slurry dries. While drying occurs, fibrils deposit onto the tube. More slurry can be applied to the tube to add to matt thickness. When all fibrils have dried, the matt is removed as a seamless product from the tube. If reinforcement of the tubular matt is desired, fibers, bundles of fibers or fabrics can be positioned in the tube before or while the slurry is applied to the tube. These methods also apply to matts cast in other shapes, such as spheres, where the rolling would occur in more than one direction.

In a vascular prosthesis, the matt would become the inner layer inside of which the endothelial cells would be seeded. A single density foam would be cast around the matt for the ablumenal substrate for the smooth muscle cells and adventitial fibroblasts.

Ligament implants, as multifilament forms of the biopolymers of the invention, can be enhanced with the matt, matt composites, and matt compositions of the invention to promote cell seeding. For example, continuous ligament multifilament structures can be produced with or without the addition of extracellular matrix particulates, to have selected characteristics. Ligament cells can then be delivered to the ligament which can be embedded in a matt casing. The ligament can then be mounted in a tubular tissue maturation chamber. After the ligament cells have attached to the ligament, the ligament is subjected to a regime of cyclical axial elongation resulting in stress, which is increased in magnitude as the ligament matures. The mature biopolymer ligaments can be used, for example, as ligament prostheses.

Dental implants can be formed from the matt, matt composites, and matt compositions of the invention. For example, the matt, matt composites, and matt compositions can be prepared as specialized dental implants for periodontal ligament repair and bone rebuilding. In one embodiment, the matt, matt composites, and matt compositions of the invention are prepared as apron shaped implants which can be fixed to a tooth by tying the strings of the apron around the tooth. In another embodiment, the matt, matt composites, and matt compositions are designed as covers of post extraction sockets filled with bone replacement material or collagen composition. In yet another embodiment, the matt, matt composites, and matt compositions are designed as bone replacement material-filled tubes to serve as alveolar ridge builders.

The apron shaped matt, which can be produced as a matt with low porosity or a matt composition including a double density or quadruple density foam, i.e., a double density foam folded over on itself, for promoting periodontal ligament repair and bone rebuilding can be positioned between a gum flap and the alveolar bone in the area requiring periodontal ligament repair and bone rebuilding. The matt can be designed to block invasion by junctional epithelium of the cleaned and planed tooth zone. Periodontal ligament cells can then migrate into the matt, matt composite, or matt composition, bind to the matt, matt composite, or matt composition, and secrete extracellular matrix products into the matt, matt composite, or matt composition. The matt, matt composite, or matt composition can also be invaded by capillary endothelial cells and immune cells which provide defense against microbial assault. By excluding epithelium and by stimulating periodontal ligament cells, the matt, matt composite, or matt composition can promote regeneration of periodontal ligament and alveolar bone. The apron shaped dental implants can also be modified to include a bone replacement material as described herein. In one embodiment, the material can be included in an outpocketing of the apron which can be placed on the eroded alveolar bone. The bone replacement material provides pathways for invading bone cells. The apron shaped dental implant can also include extracellular matrix particulates generated from dental tissues. These extracellular matrix particulates provide the appropriate growth factors, e.g., bone and ligament specific growth factors, for promoting periodontal ligament cell and bone cell growth into the implant.

Alternatively, the matt, matt composites, and matt compositions of the invention can be prepared as post extraction socket covers. The matt can be used to cover the socket filler material which is inserted into sockets of extracted teeth. These socket fillers promote bone regeneration within the socket which, at a minimum, provides a foundation for a metal, e.g., titanium, fixture and subsequent application of a crown. The titanium or other material fixture can be anchored in a socket immediately after an extraction with calcium phosphate bone replacement material reinforced and covered or "tented" with one of the matt, matt composites, or matt compositions described herein as an apron. The socket fillers can also include extracellular matrix particulates generated from bone tissue or dental papilla. These extracellular matrix particulates provide the appropriate growth factors, e.g., bone specific growth factors, for promoting bone cell growth into the implant. In addition, in instances where the bony foundation for dental implants composed of metal does not provide adequate support for the metal implant, bone replacement material reinforced or strengthened with the foams and foam compositions of the invention can be used to reinforce the bony foundation.

In yet another embodiment, the matt, matt composites, and matt compositions can be designed as alveolar ridge substitutes or alveolar ridge builders. Alveolar ridge substitutes are used to provide underpinning for dentures. Typically, the alveolar ridge substitutes are designed as biopolymer matt tubes of the appropriate length which are filled with non-resorbable calcium phosphate bone replacement material to build up a mineralized platform along the alveolar ridge and to promote development of bone and a connective tissue framework around the calcium phosphate particles. The alveolar ridge builders of the invention have the same design as that of the alveolar ridge substitutes except that the matt tube is filled with resorbable forms of bone replacement material to promote bone development. The composition of the alveolar ridge builders promotes bone cell and blood capillary penetration leading to regrowth and restoration of the ridge prior to, for example, installation of a denture or a metal implant. The matt tube of the alveolar ridge builder can also include extracellular matrix particulates which promote alveolar ridge bone regeneration.

Similarly, the matt, matt composites, and matt compositions of the invention enriched, for example, with extracellular matrix particulates derived from organs e.g., cardiac tissue, bladder tissue, tissue from the small intestine, lung tissue, pancreatic tissue, hepatic tissue, skin tissue, and other organ tissue, can be seeded with analogous organ cells such as those of the endocrine pancreas, e.g., pancreatic islet cells, or those of the liver, e.g., hepatocytes, as means of promoting cell proliferation before and/or after implantation so that after implantation and vascularization of the cell-laden matt implant, a functional replacement organ develops.

Examples of cell types which have been successfully grown in and on the matt and matt compositions of the invention include mesenchymal cells, dermal fibroblasts, keratinocytes, osteoblasts, gingival fibroblasts, and tendon and ligament cells.

This invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLE 1

PRODUCTION OF MATT FROM COLLAGEN EXTRACTED FROM SKINS OF PORCINE FETUSES

Five ml of 5 mg/ml collagen was diluted with 20 ml of 30 mM sodium phosphate pH 7.4 on ice. The pH was adjusted to 7.4 with 5% ammonium hydroxide and the final volume was adjusted to 30 ml with the phosphate buffer. The solution was mixed end-over-end for 2 h at 4° C. The solution, in one batch was poured over a 270-mesh stainless steel screen (~50 $\mu$m pore size) and the resulting 2 mm thick fibril-gel was dried at 30° C. for 16 h. The matt, after being peeled from the screen, without further manipulation, had a wet tensile strength of 0.03 MPa and a 1 $cm^2$ piece resisted the digestion by IOU of collagenase for much more than 22 h and by 6.4 U of elastase for more than 25 h at 37° C. The addition of 0.1 M NaCl to the dilution buffer resulted in a predominantly fibril (little gel) matt with 0.5 Mpa strength.

EXAMPLE 2

COLLAGENASE RESISTANT PROPERTIES OF MATT

Collagenase resistance properties of the matt are calculated by computing the time for digestion per mg of collagen scaffold. A matt digested in collagenase at the rate of 87 min per mg collagen, while two styles of double density foam both digested at the rate of 25 min per mg collagen scaffold. Therefore, collagen matt is more than three times as resistant to collagenase digestion as collagen scaffolds of similar density, which themselves are three times more resistant to digestion as single density foams.

EXAMPLE 3

FORMATION OF MATT COMPOSITES

Collagen fibrils were formed and their collection accelerated by centrifugation. The collagen fibril slurry was resuspended and deposited onto a screen. Residual solution was allowed to drain through the screen for 15 min. then a 1% gelatin solution was layered onto the collagen collection. The material was allowed to dry, during which time, the two biopolymer component layers fused. After drying, the matt composite was removed from the screen for examination of its tensile properties. This matt had lower strength than a control matt, but the strain was greater than the control matt. The layering sequence can be reversed. In other words, this example illustrates how the elasticity of the matt can be manipulated.

EXAMPLE 4

MANIPULATION OF MATT TEAR PROPERTIES 5 ml of collagen fibril/fibril bundle slurry was mixed with 0.03 g of calcium sulfate particles of the size 140 $\mu$m to 400

µm. The combined slurry was applied to a porous support and allowed to dry. The resulting matt had single calcium sulfate particles or clumps of two to five particles spaced 200 to 700 µm from each other.

EXAMPLE 5

DERMAL FIBROBLAST CELL GROWTH ON MATT

Human dermal fibroblasts were suspended at $5 \times 10^5$ cells/ml in Dulbecco's minimum essential medium plus 5% bovine serum. Matts were hydrated in this medium. The cell suspension was added dropwise to 1 cm² of the matt and then the cells were allowed to attach. After allowing for cell attachment, additional medium was added and the matts were allowed to incubate at 37° C. for 24 h. The cells exhibited the normal spindle shaped fibroblastic morphology at this time when observed by fluorescence microscopy. In addition, the cell arrangements reflected the texture of the matt surface. If the matt surface was flat, the fibroblasts were uniformly distributed over the matt surface. If the matt surface was textured, the distribution of the fibroblasts reflected the texture pattern. The cells aligned within and along grooves.

EXAMPLE 6

KERATINOCYTE CELL GROWTH ON MATT

Keratinocytes were seeded onto matts at a density of $1 \times 10^5$ cells per cm² in keratinocyte growth medium. After three days of cultivation in this medium, the matts were fixed for histological analysis. Keratinocytes had attached, were healthy, and had proliferated to form multiple layers characteristic of this cell type.

EXAMPLE 7

CYTOTOXICITY EVALUATION OF MATT

Extracts were prepared of sterilized and non-sterilized matts in cell culture media and fed to sub-confluent cultures of dermal fibroblasts to assess toxicity of leachables from the matts. Using a method based on USP guidelines, extracts were prepared by placing 60 cm² of sample in 30 ml of media (DMEM 5% serum) and incubated for 24 hours at 37° C. Extract-media was passed through a 0.22 micron filter for sterilization this extract-media was fed to sub-confluent (approximately 80% confluency) fibroblast cultures and examined after 48 hours. In all cultures, cells grew to confluency (cell proliferation was not inhibited by the extract) and cell morphology appeared identical to control cultures (those fed with DMEM+5% serum). These results are indicative of a non-cytotoxic material.

EXAMPLE 8

EFFECT OF UV TREATED MATT

Matts dried onto a screen were treated by exposure to 254 nm ultraviolet light, 20 minutes per side. The wet tensile strength of the treated matt was 2.6 MPa, compared to 0.27 MPa for a control sample which was not treated with UV light.

EXAMPLE 9

INCLUSION OF LIVING CELLS DURING MATT PRODUCTION

Biopolymer fibrils were formed by diluting collagen to 1 mg/ml in Dulbecco's minimum essential medium (DME), using 5% ammonium hydroxide to adjust the pH to 7.4, and mixing the solution for 3.5 h at 4° C. This fibril solution was used to resuspend dermal fibroblasts to a concentration of $3 \times 10^6$ cells per ml. This cell/fibril solution was placed in a tissue culture insert with a 0.4 µm pore polycarbonate membrane alone or also containing a single density foam. The inserts were placed in a multiwell tissue culture dish with additional DME and the dishes were incubated for cell growth. On days 1 and 7, the inserts were removed and processed for histological analysis which showed that fibrils and healthy cells were intermingled in the layer above the insert membrane or the foam.

EXAMPLE 10

SEQUENTIAL ACID AND ENZYME EXTRACTION OF COLLAGEN FROM SKIN OF PORCINE FETUSES

The preferred forms of collagens used to produce biopolymer fibrils for the biopolymer matts are the acid extracted fetal porcine collagens purified as in example 11. Additional, less preferred forms of fetal porcine collagens can be purified for use in the production of biopolymer matts through enzymatic digestion of the residual skins after collection of the acid collagen extract for example 11. The collagens, from many of which one or both telopeptides are removed, leaving some of the molecules with only their triple helical portions or with one telopeptide plus the triple helical portion, are extracted by mixing the residual skins for two sequential five to seven day periods (in the cold as are all the following steps) in 0.017% pepsin in extraction buffer at a proportion of one volume skin to two volumes solution. The two pepsin extracts are collected, combined and clarified through continuous flow centrifugation at 13,000 rpm, 40 ml/min. The pepsin extracted collagen then is purified by the same method as the acid extracted collagen, except the solution volume is not reduced before dispersal of the first collagen precipitate, the second NaCl addition is only to 0.7M, the filtration only goes down to 3.0 µm, the hollow fiber pore size has a cut off of 100,000 Da, and the concentration reached in the hollow fiber is 6 to 9 mg/ml.

As determined by polyacrylamide gel electrophoresis, the acid extracted collagen is a mixture of fetal collagens including collagen type I, collagen type III, and collagen type IV. The pepsin extracted collagen, i.e., slightly clipped collagen, contains the triple helical cores without the telopeptides of the mixed collagens except for lower amounts of type IV, which is subject to degradation with the enzyme treatment. Collagen concentrations also are determined by hydroxyproline assay standards. Protein identities and integrity are validated by polyacrylamide gel electrophoresis and viscosity is standardized at 5 mg/ml at a minimum of 50 centipoise. Both acid and pepsin extracted fetal porcine collagens of Examples 11 and are able to form a gel at neutral pH. The absence of denatured contaminants is measured by polarity (values at −350° and lower are acceptable). Quality is also tested by the ability of the collagen to form fibers.

EXAMPLE 11

ACID EXTRACTION OF COLLAGEN FROM SKIN OF PORCINE FETUSES

Preferred molecules used to produce biopolymer fibrils for the matt are collagens. The preferred source of collagens is fetal porcine skin. Collagens are purified from those skins by methods standard to those skilled in the art as follows: The fetal porcine skins are obtained by skinning 70% ethanol-dipped near term fetuses after their aseptic removal from a partially thawed, bleached and rinsed porcine uterus. The skins and collagen solutions are kept cold for all the following procedures. The skins are ground and then washed in batches of 5 kg with multiples of 5 liters of ⅓×PBS, with the waste wash solution removed by filtering the skins with layered cheesecloth. The collagen is extracted from the washed skin over seven days with extraction buffer, 0.5M acetic acid and 2 mM EDTA at pH 2.5 in the proportion of 150 g skin per liter extraction buffer. On the eighth day, the extract is collected after filtration from the skin through cheesecloth and sodium chloride is added to the extract to bring the solution to 0.9M NaCl. The collagen precipitates out of this solution over the next two hours while the solution is stirring. The precipitated collagen is collected as a pellet through continuous flow centrifugation at 12,000 rpm and 300 ml/min. The supernatant is discarded and the pellet is dispersed in 60% of the original volume of extraction buffer. After allowing the pellet to redissolve by stirring overnight in this solution, the collagen is reprecipitated with NaCl to 0.9M for 2 h and collected again as a pellet through continuous flow centrifugation. This pellet is dispersed and redissolved in the same volume of extraction buffer as the first pellet. After allowing the pellet to redissolve by stirring overnight in this solution, the collagen is clarified by continuous flow centrifugation at 15,000 rpm and 40 ml/min. The pellet is discarded and the collagen supernatant is filtered through filters down to 2.0 $\mu$m. The collagen concentration is then determined with a hydroxyproline assay. The solution then is dialyzed by sequential concentration steps in a 0.1 $\mu$m hollow fiber filter followed by dilution with deionized water, repeated until the acetic acid concentration reaches 0.05M. Once this acetic acid concentration is reached, the collagen solution is concentrated to 5 to 7 mg/ml in the hollow fiber. The final concentration of collagen is then confirmed with a hydroxyproline assay.

Equivalents

Those skilled in the art will recognize, or be able to ascertain using no more than routine experimentation, many equivalents to specific embodiments of the invention described specifically herein. Such equivalents are intended to be encompassed in the scope of the following claims.

What is claimed is:

1. A resorbable nonporous biopolymer matt comprising a densely packed random array of biopolymer fibrils.

2. The biopolymer matt of claim 1, wherein said biopolymer fibrils are selected from the group consisting of collagen, laminin, elastin, fibronectin, fibrinogen, thrombospondin, gelatin, polysaccharides, poly-1-amino acids and combinations thereof.

3. The biopolymer matt of claim 1, wherein said biopolymer fibrils are derived from collagen.

4. The biopolymer matt of claim 3, wherein said collagen is fetal porcine collagen.

5. The biopolymer matt of claim 1, wherein said biopolymer matt further comprises macromolecules necessary for cell growth, morphogenesis, differentiation, or tissue building and combinations thereof.

6. The biopolymer matt of claim 1, wherein the biopolymer fibrils are crosslinked.

7. The biopolymer matt of claim 1, further including a resorbable polymer selected from the group consisting of fibers, braids, bundles of fibers, fabrics and nonwoven fabrics.

8. The biopolymer matt of claim 1, wherein said biopolymer further includes pores.

9. The biopolymer matt of claim 1, wherein said matt is in or on a support.

10. The biopolymer matt of claim 9, wherein said support is porous.

11. The biopolymer matt of claim 10, wherein said biopolymer matt is bound to a single density biopolymer foam comprising a network of communicating microcompartments having biopolymer molecules and/or biopolymer filaments interspersed within the wall of the microcompartments, wherein the microcompartments:

have volume dimensions of x, y, and z, wherein x=length, y=width, and z=height, are substantially equal, and range from about 1 $\mu$m to about 300 $\mu$m; and have an average wall thickness of less than about 10 $\mu$m.

12. The biopolymer matt of claim 11, wherein said biopolymer foam is derived from fetal porcine collagen.

13. The biopolymer matt of claim 1, wherein said biopolymer matt further comprises cells.

\* \* \* \* \*